United States Patent
Zamft

(10) Patent No.: US 12,131,806 B2
(45) Date of Patent: Oct. 29, 2024

(54) METHODS AND COMPOSITIONS FOR APPLYING MACHINE LEARNING TO PLANT BIOTECHNOLOGY

(71) Applicant: X Development LLC, Mountain View, CA (US)

(72) Inventor: Bradley Michael Zamft, Mountain View, CA (US)

(73) Assignee: X Development LLC, Mountain View, CA (US)

(*) Notice: Subject to any disclaimer, the term of this patent is extended or adjusted under 35 U.S.C. 154(b) by 0 days.

(21) Appl. No.: 18/208,207

(22) Filed: Jun. 9, 2023

(65) Prior Publication Data

US 2023/0317210 A1 Oct. 5, 2023

Related U.S. Application Data

(63) Continuation of application No. 16/853,297, filed on Apr. 20, 2020, now Pat. No. 11,763,916.

(Continued)

(51) Int. Cl.
*G16B 40/00* (2019.01)
*C12N 5/04* (2006.01)
(Continued)

(52) U.S. Cl.
CPC .............. *G16B 40/00* (2019.02); *C12N 5/04* (2013.01); *G06N 3/044* (2023.01); *G06N 3/047* (2023.01); *G16H 50/20* (2018.01)

(58) Field of Classification Search
CPC ........ G16B 40/00; G16H 50/20; G06N 3/047; G06N 3/044; C12N 5/04
See application file for complete search history.

(56) References Cited

U.S. PATENT DOCUMENTS

2003/0148309 A1* 8/2003 del Cardayre ..... C12N 15/1027
435/325
2014/0220568 A1* 8/2014 Inze .................. G16B 5/00
435/6.11
(Continued)

FOREIGN PATENT DOCUMENTS

EP 3474167 4/2019

OTHER PUBLICATIONS

Hu et al., "Accumulation of medium-chain, saturated fatty acyl moieties in seed oils of transgenic Camelina sativa," PLoS One, Feb. 2017, 12:1-14.
(Continued)

*Primary Examiner* — Khai M Nguyen
(74) *Attorney, Agent, or Firm* — Fish & Richardson P.C.

(57) ABSTRACT

Methods, systems, and apparatus, including computer programs encoded on computer storage media, for using machine learning models for plant biotechnology. One of the methods includes obtaining a network input comprising an image depicting a plurality of plant cells or regions of plant tissue; processing the network input using a machine learning model to obtain an identification of one or more particular biotechnologically-modifiable plant cells or one or more particular biotechnologically-modifiable regions of the plant tissue; excising or delineating the one or more identified plant cells or the one or more identified regions of the plant tissue; and delivering exogenous material to the excised or delineated plant cells or regions of plant tissue.

20 Claims, 7 Drawing Sheets

Related U.S. Application Data

(60) Provisional application No. 62/836,424, filed on Apr. 19, 2019.

(51) Int. Cl.
  G06N 3/044 (2023.01)
  G06N 3/047 (2023.01)
  G16H 50/20 (2018.01)

(56) References Cited

U.S. PATENT DOCUMENTS

| | | | | |
|---|---|---|---|---|
| 2014/0283225 | A1* | 9/2014 | Samuel | C12N 15/821 |
| | | | | 800/312 |
| 2019/0050533 | A1* | 2/2019 | Brown | G16B 40/00 |
| 2019/0050948 | A1 | 2/2019 | Perry et al. | |

OTHER PUBLICATIONS

Jegou et al., "Aggregating Local Descriptors into a Compact Image Representation," 2010 IEEE Computer Society Conference on Computer Vision and Pattern Recognition, Jun. 2010, pp. 3304-3311.

Keshavareddy et al., "Methods of Plant Transformation—A Review," International Journal of Current Microbiology and Applied Sciences, Jul. 2018, pp. 2656-2668.

Lenaghan et al., "An Automated Protoplast Transformation System," Plant Genome Editing with CRISPR Systems, Jan. 2019, pp. 355-363.

Lowe, "Distinctive Image Features from Scale-Invariant Keypoints," International Journal of Computer Vision, Nov. 2004, pp. 91-110.

Orcutt, "The Quest to Engineer the Perfect Potato," Jun. 5, 2015, retrieved on Jun. 11, 2020, retrieved from URL <https://www.technologyreview.com/2015/06/05/110372/the-quest-to-engineer-the-perfect-potato/>, 7 pages.

Roest et al., "Plant Regeneration from Protoplasts: A Literature Review," Acta Bot. Neerl., Mar. 1989, pp. 1-23.

Sanchez et al., "Image Classification with the Fisher Vector: Theory and Practice," International Journal of Computer Vision, Jun. 2013, 24 pages.

Shen et al., "Driving Forces Enable High-Titer Anaerobic 1-Butanol Synthesis in *Escherichia coli*," Applied Environmental Microbiology, May 2011, 77(9):2905-2915.

Wan et al., "Generation of Large Numbers of Independently Transformed Fertile Barley Plants," Plant Physiology, Jan. 1994, 104:37-48.

Zhu et al., "Combinatorial genetic transformation generates a library of metabolic phenotypes for the carotenoid pathway in maize," PNAS, Nov. 2008, 105(47):18232-18237.

* cited by examiner

METHODS AND COMPOSITIONS FOR APPLYING MACHINE LEARNING TO PLANT BIOTECHNOLOGY

CROSS-REFERENCE TO RELATED APPLICATIONS

This application is a continuation of and claims priority to U.S. patent application Ser. No. 16/853,297, filed on Apr. 20, 2020, which claims the benefit of U.S. Provisional Application Ser. No. 62/836,424, filed on Apr. 19, 2019, the entire contents of which are hereby incorporated by reference.

BACKGROUND

This specification relates to applications of neural networks, and more particularly to techniques of applying neural networks to plant biotechnology.

Neural networks, or for brevity, networks, are machine learning models that employ multiple layers of operations to predict one or more outputs from one or more inputs. Neural networks typically include one or more hidden layers situated between an input layer and an output layer. The output of each layer is used as input to another layer in the network, e.g., the next hidden layer or the output layer.

Each layer of a neural network specifies one or more transformation operations to be performed on input to the layer. Some neural network layers have operations that are referred to as neurons. Each neuron receives one or more inputs and generates an output that is received by another neural network layer. Often, each neuron receives inputs from other neurons, and each neuron provides an output to one or more other neurons.

An architecture of a neural network specifies what layers are included in the network and their properties, as well as how the neurons of each layer of the network are connected. In other words, the architecture specifies which layers provide their output as input to which other layers and how the output is provided.

The transformation operations of each layer are performed by computers having installed software modules that implement the transformation operations. Thus, a layer being described as performing operations means that the computers implementing the transformation operations of the layer perform the operations.

Each layer generates one or more outputs using the current values of a set of parameters for the layer. Training the neural network thus involves continually performing a forward pass on the input, computing gradient values, and updating the current values for the set of parameters for each layer using the computed gradient values. Once a neural network is trained, the final set of parameter values can be used to make predictions in a production system.

SUMMARY

This specification describes how a plant biology system can use one or more machine learning models to determine an optimal process for biotechnologically modifying one or more plant cells or plant tissue. For example, the plant biology system can use the machine learning models to determine an optimal process for delivering exogenous material to the plant cells or plant tissue, e.g., genetically engineering the plant cells or plant tissue, editing the RNA of the plant cells or plant tissue, or delivering proteins or other biomolecules to the plant cells or plant tissue.

Using techniques described in this specification, a plant biology system can produce new or existing crops or cultivars, e.g., recombinant and/or genetically-engineered crops and cultivars, in a high-throughput manner. In this specification, a process is "high-throughput" if the process leverages automation and/or machine learning to generate many target outputs in a large-scale manner.

As a particular example, a plant biology system can use one or more machine learning models to select one or more plant cells or one or more regions of plant tissue to biotechnologically modify, e.g., by processing images of multiple candidate plant cells or candidate regions of plant tissue using an image processing machine learning model configured to select particular plant cells or regions of tissue that are likely to be engineerable.

Instead or in addition, the plant biology system can use one or more machine learning models to select a particular technique by which the plant biology system will biotechnologically modify the selected plant cells or regions of plant tissue.

Instead or in addition, the plant biology system can use one or more machine learning models to select one or more biotechnologically modified plant cells or regions of plant tissue for regeneration, e.g., by processing images of multiple biotechnologically modified plant cells or regions of plant tissue using an image processing machine learning model configured to select particular biotechnologically modified plant cells or regions of tissue that are likely to successfully regenerate.

Instead or in addition, the plant biology system can use one or more machine learning models to select a particular technique by which the plant biology system will grow one or more regenerated plants, plantlets, or plant tissue into a full plant.

Particular embodiments of the subject matter described in this specification can be implemented so as to realize one or more of the following advantages.

Some existing high-throughput techniques have been developed for single cell organisms, e.g., for genetically engineering single cell organisms. However, these high-throughput techniques have not translated to most plant biotechnology applications, especially to crop plants. Using techniques described in this specification, a system can increase the capacity and speed of plant biotechnology processes. Furthermore, these techniques can be used to biotechnologically modify crops and cultivars that traditionally have been recalcitrant to modification, e.g., recalcitrant to plant breeding techniques, tissue culture, and transformation.

Traditionally, biotechnologically modifying plants, e.g. by transforming plant cells, has been an "artisanal" process; that is, for many specific processes, only a few experts of the field are able to perform the specific process, and sometimes even the experts do not have a concrete rubric for executing the process, but rather rely on instinct. For example, experts in developing transgenic soy plants often look for specific visual properties in the callus, such as translucency, friability, glossiness, etc. Additionally, many experts rely on custom chemical components in culturing media. However, the use of genes that encode plant developmental regulators has recently shown to have the potential to enable a universal plant biotechnological modification process. Genes such as WUSHEL were identified in model plant systems as controlling the vegetative to embryonic transition in plant cells, allowing the conversion of common leaf cells into undifferentiated totipotent cells. Orthologous have been demonstrated in specialty crops that had previously been highly recalcitrant to induce somatic embryogenesis. Because they have the ability to readily grow into whole plants, embryonic cells are one of the best sources of explant material for genetic transformation or biotechnological modifications. Combinations of Baby Boom and Wushel have been utilized to dramatically improve the efficiency of transformation of both specialty and major row crops. The genetic networks by which these developmental regulators induce embryogenesis are beginning to be understood, and will differ between plant species to most efficiently generate embryonic tissue. Using techniques described in this specification, a system can develop modification procedures and cell culture techniques for a given plant or plant cultivar into a more directed and formalized process, thereby improving efficiency and consistency.

Techniques described in this specification can be used to increase the pace at which plant science experiments are performed, i.e., increase the pace of the design-build-test-learn cycle, by multiple orders of magnitude. For example, combinatorial metabolic pathways can be used to generate crops with properties that cannot be obtained using traditional breeding or even gene editing techniques. As another example, combinations of mutations arising from gene edits can also be tested at a dramatically increased rate.

As used herein:
a locus refers to a region, or address, within the genome;
a Single Nucleotide Polymorphism (SNP) refers to a single base within the genome that has a variation, or a polymorphism, in the population;
a causative SNP or a causative variant refers to a version of a SNP that has a specific phenotypic effect.
a quantitative trait locus (QTL) refers to a locus on the genome that is associated with a quantitative phenotype.
expression QTL (eQTL) refers to a QTL that is associated with a change in expression of a particular gene.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes how a system can use machine learning models and automation to determine a process for performing biotechnological modifications to plant cells or plant tissue. Using the techniques described in this specification, a system can modify plant cells or plant tissue in a high-throughput manner.

Figure 1:
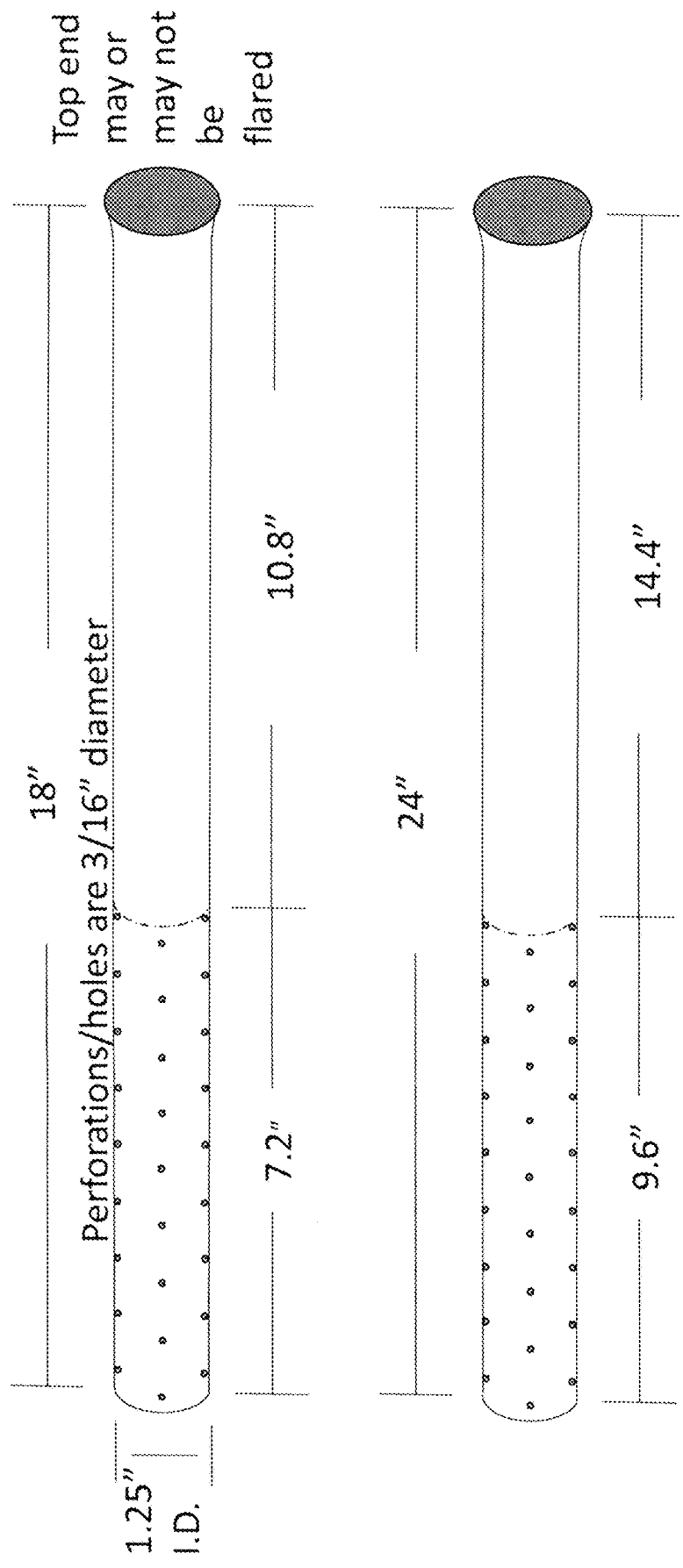
FIG. 1 is a diagram of an example high-throughput plant biology system.

FIG. 1 is a diagram of an example high-throughput plant biology system 100. The plant biology system 100 is an example of a system implemented as computer programs on one or more computers in one or more locations in which the systems, components, and techniques described below are implemented.

The high-throughput plant biology system 100 is configured to receive system inputs 102 that characterize i) candidate plant cells or plant tissue and ii) one or more desired biotechnological modification to the plant cells or tissue, e.g., genetic engineering, RNA insertion or deletion, CRISPR genome editing, etc. For example, the system inputs 102 can include data characterizing one or more of: how the plants that generated the plant cells or tissue were grown, how the plant tissue was processed, including any potential pre-treatment (e.g. staining) of the tissue, any other data collected on the cells or plant tissue or regions therein (e.g. molecular data), or regions defined by users. For example, the system inputs 102 can include one or more images that depict the candidate plant cells or plant tissue. The high-throughput plant biology system 100 can process the system inputs 102 to determine an optimal process for executing the desired biotechnological modifications on the plant cells or plant tissue to generate engineered and regenerated plants 192.

The high-throughput plant biology system 100 includes a cell/tissue identification system 100, which is configured to receive the system inputs 102 and process the system inputs 102 to generate a selection of cells and regions of tissue 112. The selection of cells or regions of tissue 112 identifies one or more cells or regions of tissue from the multiple candidate cells or regions of tissue that are available to the high-throughput plant biology system 100. The selected cells or regions of tissue 112 will be biotechnologically modified in accordance with a process determined by the high-throughput plant biology system 100 in order to generate the engineered and regenerated plants 192.

The cell/tissue identification system 110 can include one or more machine learning models to determine the selected cells or regions of tissue 112 from the candidate cells or tissues. The process for determining the selection of cells or regions of tissue 112 for biotechnological modification from a set of candidate cells or regions of tissue is discussed in more detail below in reference to FIG. 2.

The cell/tissue identification system 110 can provide the selection of plant cells or regions of tissue 112 to a modification protocol identification system 120 of the high-throughput plant biology system 100. The modification protocol identification system 120 can include one or more machine learning models that are configured to process i) data characterizing the one or more desired biotechnological modifications in the system inputs 102, ii) data characterizing the selected plant cells or regions of tissue 112, e.g., one or more images depicting the selected plant cells or regions of tissue 112, or iii) both, in order to determine a biotechnological modification protocol 122. The biotechnological modification protocol 122 defines one or more techniques and/or apparatus that are to be used to perform the desired biological modifications to the selected plant cells or regions of plant tissue 112. The process for determining a biotechnological modification protocol 122 is discussed in more detail below in reference to FIG. 3.

The modification protocol identification system 120 can provide the biotechnological modification protocol 122 to a modification engine 130 that can orchestrate the execution of the biotechnological modification protocol 122 on the selected plant cells or regions of tissue 112 using any number of automated and/or robotic systems (e.g., from dissection to changing media to the biotechnological modification), generating biotechnologically modified cells or tissue 132. For example, the modification engine 130 can send instructions to one or more apparatus identified in the biotechnological modification protocol 122, causing the apparatus to perform the biotechnological modification protocol 122. As a particular example, the modification engine 130 can generate a robotic or automated control plan according to the biotechnological modification protocol 122, and send instructions to a control system that is configured to control one or more robotic or automation components. The control system can then execute the control plan generated by the modification engine 130 by issuing commands to the robotic or automated components in order to drive the movements of the components. The robotic components can include, for example, one or more robotic arms for dissecting or transferring the selected plant cells or regions of plant tissue 112 to different media or for transferring the biotechnologically modified cells or tissue 132 to different media, and/or one or more lasers for dissection of the selected plant cells or regions of plant tissue 112 or the biotechnologically modified cells or tissue 132.

After orchestrating the execution of the biotechnological modification protocol 122, the modification engine 130 can provide data characterizing the generated biotechnologically modified cells or tissues 132 to a modification analysis system 140. The modification analysis system 140 is configured to process the data characterizing the biotechnologically modified cells or tissues 132 and determine a measure of success of the biotechnological modification protocol 122 at modifying the selected cells or regions of tissue 112. For example, the modification analysis system can determine a modification efficiency 142, i.e., a proportion of the selected cells or regions of tissue 112 that were "successfully" modified to generate a biotechnologically modified cell or region of tissue 132, according to a predetermined measure of success.

In some implementations, the modification analysis system 140 can include one or more machine learning models that are configured to process the data characterizing the biotechnologically modified cells or tissue 132 to generate a prediction of the modification efficiency 142. In some other implementations, the modification analysis system 140 can be configured to process the data according to one or more curated criteria, and calculate the modification efficiency according to the curated criteria. For example, the criteria can be defined as a dsRed signal, or any equivalent visual marker.

As a particular example, the data characterizing the biotechnologically modified cells or tissue 132 can include one or more images of the biotechnologically modified cells or tissue, and the modification analysis system 140 can process the images, e.g., using a convolutional neural network, to generate a prediction of the modification efficiency 142. The convolutional neural network can be trained using a labeled training data set that includes multiple images depicting respective biotechnologically modified cells or regions of tissue, where a label corresponding to each image identifies whether or not the biotechnologically modified cell or region of tissue exceeds a particular quality threshold. Other example of data characterizing the biotechnologically modified cells or tissue 132 that can be processed by a machine learning network to determine the modification efficiency 142 is described in more detail below in reference to FIG. 4.

As another particular example, the modification analysis system 140 can process the data characterizing the biotechnologically modified cells or tissue to determine a measure of fitness of each biotechnologically modified cell or tissue. The measure of fitness of a plant cell or region of plant tissue, e.g., a value between 0 and 1, can characterize the healthiness, robustness, or vigor of the plant cell or tissue. The measure of fitness of a plant cell or tissue can be evaluated using, for example, morphology, color, size, metabolic activity, or rate of cell division or differentiation. These can be compared to define "normal" plant cells or tissues. The modification analysis system 140 can then determine the modification efficiency by determining a proportion of biotechnologically modified cells or regions of tissue whose predicted fitness exceeds a particular threshold, e.g., 0.5, 0.9, or 0.95. Determining a measure of fitness of a cell or region of tissue is discussed in more detail below in reference to FIG. 6.

The high-throughput plant biology system 100 can use the modification efficiency 142 to train or fine-tune the machine learning models of the cell/tissue identification system 110 and/or the modification protocol identification system 120. For example, the high-throughput plant biology system 100 can use the modification efficiency 142 as a reinforcement learning objective function for one or more machine learning models in the cell/tissue identification system 110 and/or the modification protocol identification system 120. That is, the high-throughput plant biology system 100 can have a training subsystem that trains the machine learning models of the systems 110 and 120 to maximize the modification efficiency 142, e.g., by generating a parameters update for the machine learning models using the modification efficiency 142 and back-propagating the update through the machine learning models.

Continuing the biotechnological modification process, the modification engine 130 can also provide the data characterizing the biotechnologically modified cells or tissue 132 to a cell/tissue regeneration identification system 150 in the high-throughput plant biology system 100. The cell/tissue regeneration identification system 150 can include one or more machine learning models that are configured to process i) data characterizing the one or more desired biotechnological modifications in the system inputs 102, ii) data characterizing the biotechnologically modified cells or tissue 132, e.g., one or more images depicting the cells or tissue 132, or iii) both, in order to generate a selection of biotechnologically modified cells or regions of tissue 152. The selection of cells or regions of tissue 152 identifies one or more of the biotechnologically modified cells or regions of tissue 132 that will be regenerated by the high-throughput plant biology system 100. The process for determining a selection of biotechnologically modified cells or regions of tissue 152 is discussed in more detail below in reference to FIG. 4.

In some implementations, the cell/tissue regeneration identification system 150 also determines a particular regeneration protocol for regenerating the selected cells or tissue 152. That is, the cell/tissue regeneration identification system 150 can include one or more machine learning models that are configured to process i) data characterizing the one or more desired biotechnological modifications in the system inputs 102, ii) data characterizing the biotechnologically modified cells or tissue 132, or iii) both, in order to determine a particular regeneration protocol for regenerating the selected biotechnologically modified cells or regions of tissue 152. For example, the cell/tissue regeneration identification system can define one or more techniques and/or apparatus that are to be used to regenerate the selected cells or regions of plant tissue 152. This can include the induction of expression of transgenes such as developmental regulators.

The cell/tissue regeneration identification system 150 can provide the selection of the biotechnologically modified cells or regions of tissue 152 to a regeneration engine 160 that can orchestrate the regeneration of the selected biotechnologically modified cells or regions of tissue 152 using any number of automated or robotic systems, generating regenerated cells, tissues, or plantlets 162 in a high-throughput manner. For example, regeneration engine 160 can send instructions to one or more regeneration apparatus, causing the regeneration apparatus to regenerate the selected cells or tissue 152. As a particular example, the regeneration engine 160 can generate a robotic or automated control plan and send instructions to a control system that is configured to control one or more robotic or automation components. The control system can then execute the control plan generated by the regeneration engine 160 by issuing commands to the robotic or automated components in order to drive the movements of the components (e.g., laser dissection, moving or transferring the cells or tissue to different media, or separating separate regeneration events).

After orchestrating the regeneration of the selected cells or regions of tissue 152, the regeneration engine 160 can provide data characterizing the regenerated cells, tissue, or plantlets 162 to a regeneration analysis system 170. The regeneration analysis system 170 is configured to process the data characterizing the regenerated cells, tissue, or plantlets to determine a measure of success of the regeneration engine 160. For example, the regeneration analysis system 170 can determine a regeneration efficiency 172, i.e., a proportion of the selected biotechnologically modified cells or regions of tissue 152 that were "successfully" regenerated, according to a predetermined measure of success.

In some implementations, the regeneration analysis system 170 can include one or more machine learning models that are configured to process the data characterizing the regenerated cells, tissue or plantlets 162 to generate a prediction of the regeneration efficiency 172. In some other implementations, the regeneration analysis system 170 can be configured to process the data according to one or more curated criteria, and calculate the regeneration efficiency according to the curated criteria. For example, the regeneration analysis system 170 might determine the regeneration efficiency using visual analysis and counting of cells, structures such as shoots or roots, or morphology.

As a particular example, the data characterizing the regenerated cells, tissue, or plantlets 162 can include one or more images of the regenerated cells, tissue, or plantlets, and the regeneration analysis system 170 can process the images, e.g., using a convolutional neural network, to generate a prediction of the regeneration efficiency 172. As before, the convolutional neural network can be trained using a labeled training data set that includes multiple images depicting respective regenerated cells, tissue, or plantlets, where a label corresponding to each image identifies whether or not the regenerated cell, region of tissue, or plantlet exceeds a particular quality threshold. Other example of data characterizing the regenerated cells, tissue, or plantlets 162 that can be processed by a machine learning network to determine the regeneration efficiency 172 is described in more detail below in reference to FIG. 5.

As another particular example, the regeneration analysis system 170 can process the data characterizing the regenerated cells, tissue, or plantlets to determine a measure of fitness of each regenerated cell, region of tissue, or plantlet. The regeneration analysis system 170 can then determine the regeneration efficiency 172 by determining a proportion of regenerated cells, tissue, or plantlets whose predicted fitness exceeds a particular threshold, e.g., 0.5, 0.9, or 0.95.

As with the modification efficiency 142, the high-throughput plant biology system 100 can use the regeneration efficiency 172 to train or fine-tune one or more of the machine learning models or experimental techniques that precede the regeneration analysis system 170 in the high-throughput plant biology system 100, namely, one or machine learning models in the cell/tissue regeneration identification system 150, the modification protocol identification system 120, or the cell/tissue identification system 110. For example, the high-throughput plant biology system 100 can use the regeneration efficiency 172 as a reinforcement learning objective function to update the parameters of one or more machine learning models.

Continuing the biotechnological modification process, the regeneration engine 160 can provide data characterizing the regenerated cells, tissue, or plantlets 162 to a plant growth protocol identification system 180 in the high-throughput plant biology system 100. The plant growth protocol identification system 180 can include one or more machine learning models that are configured to process i) data characterizing the one or more desired biotechnological modifications in the system inputs 102, ii) data characterizing the regenerated cells, tissue, or plantlets 162, e.g., one or more images depicting the cells, tissue, or plantlets 162, or iii) both, in order to determine a plant growth protocol 182. The plant growth protocol 182 defines one or more techniques and/or apparatus that are to be used to grow the regenerated cells, tissue, or plantlets 162 into a plant as efficiently or rapidly as possible, e.g., a full plant that can survive in the field or in a greenhouse. The process for determining a plant growth protocol 182 is discussed in more detail below in reference to FIG. 5.

In some implementations, the plant growth protocol identification system 180 also identifies one or more of the regenerated cells, regions of tissue, or plantlets 162 that will be processed using the determined plant growth protocol 182. That is, the plant growth protocol identification system 180 can include one or more machine learning models that are configured to process i) data characterizing the one or more desired biotechnological modifications in the system inputs 102, ii) data characterizing the regenerated cells, tissue, or plantlets 162, or iii) both, in order to generate a selection of one or more regenerated cells, tissue, or plantlets.

The plant growth protocol identification system 180 can provide the determined plant growth protocol 182 to a plant growth engine 190 that can orchestrate the growth of the regenerated cells, tissues, or plantlets 162, to generate the engineered and regenerated plants 192. For example, the plant growth engine 190 can send instructions to one or more plant growth apparatus, causing the plant growth apparatus to grow the regenerated cells, tissue, or plantlets. As a particular example, the plant growth engine 190 can generate a robotic or automated control plan and send instructions to a control system that is configured to control one or more robotic or automation components. The control system can then execute the control plan generated by the plant growth engine 190 by issuing commands to the robotic or automated components in order to drive the movements of the components. For example, the system can move the regenerated cells, tissues, or plantlets 162 between media one or more times; instead or in addition, the system might move plantlets 162 or nascent plants to rooting soil.

After orchestrating the execution of the plant growth protocol 182, the plant growth engine 190 can provide data characterizing the engineered and regenerated plants 192 to a plant growth analysis system 194. The plant growth analysis system 194 is configured to process the data characterizing the engineered and regenerated plants 192 to determine a measure of success of the plant growth engine 190, or the high-throughput plant biology system 100 as a whole, in generating the engineered and regenerated plants 192. For example, the plant growth analysis system 194 can determine a plant growth efficiency 196, i.e., a proportion of the regenerated cells, tissue, or plantlets 162 that were "successfully" grown using the plant growth protocol 182, according to a predetermined measure of success.

In some implementations, the plant growth analysis system 194 can include one or more machine learning models that are configured to process the data characterizing the engineered and regenerated plants 192 to generate a prediction of the plant growth efficiency 196. In some other implementations, the plant growth analysis system 194 can be configured to process the data according to one or more curated criteria, and calculate the regeneration efficiency according to the curated criteria.

As a particular example, the data characterizing the engineered and regenerated plants 192 can include transcript or protein expression; specific metabolite levels; and a measure of the fitness of the engineered and regenerated plants, such as a yield of biomass, seeds or fruit of the engineered and regenerated plants; flowering time; photosynthetic efficiency; growth rate; germination rates of their seeds; photorespiratory rate; carbon fixation rate; nitrogen use efficiency; water use efficiency; abiotic stress resistance; biotic stress resistance; root growth rate; normalized differential vegetation index, or leaf area index.

As another particular example, the plant growth analysis system 194 can process the data characterizing the engineered and regenerated plants 192 to determine a measure of fitness of each engineered and regenerated plant 192. The regeneration analysis system 170 can then determine the plant growth efficiency 196 by determining a proportion of engineered and regenerated plants 192 whose predicted fitness exceeds a particular threshold, e.g., 0.5, 0.9, or 0.95.

As with the modification efficiency 142 and the regeneration efficiency 172, the high-throughput plant biology system 100 can use the plant growth efficiency 196 to train or fine-tune one or more of the machine learning models or experimental protocols that precede the plant growth analysis system 194 in the high-throughput plant biology system 100, namely, one or machine learning models in the plant growth protocol identification system 180, the cell/tissue regeneration identification system 150, the modification protocol identification system 120, or the cell/tissue identification system 110. For example, the high-throughput plant biology system 100 can use the plant growth efficiency 196 as a reinforcement learning objective function to update the parameters of one or more machine learning models.

Figure 2:
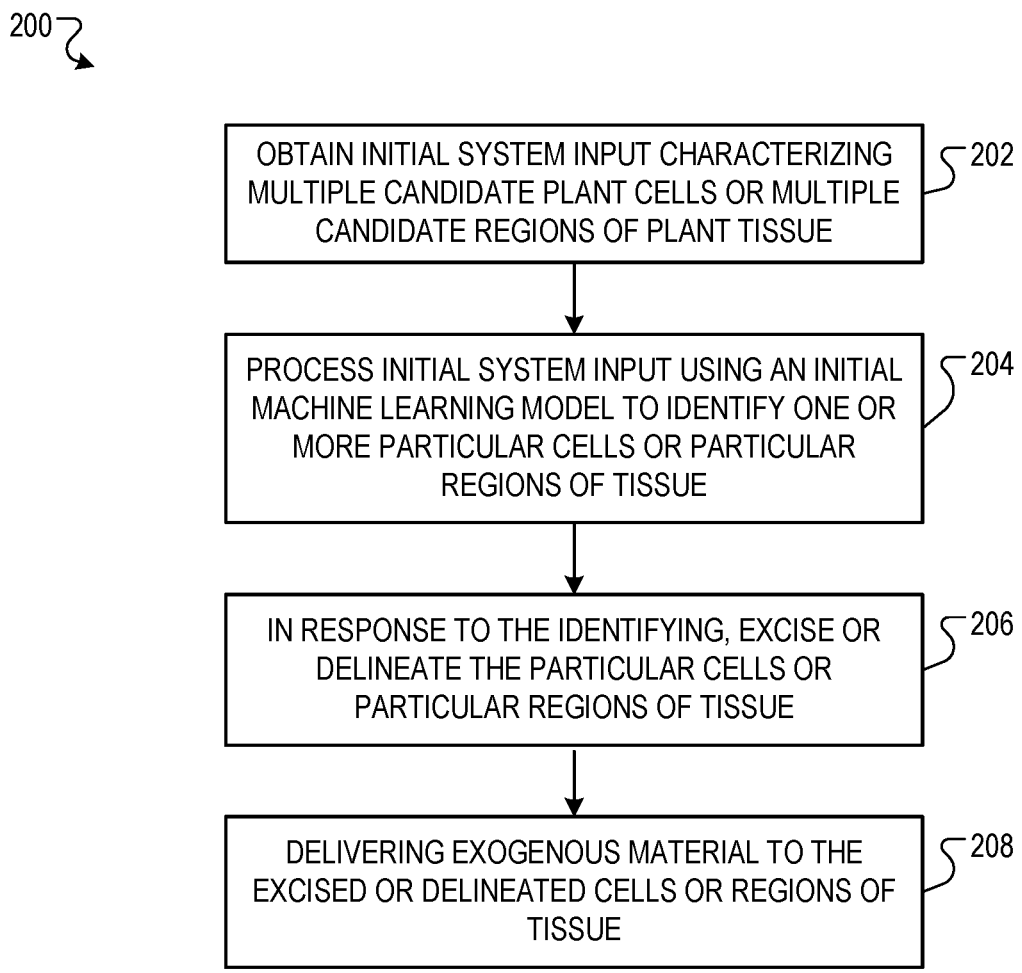
FIG. 2 is a flow diagram of an example process for identifying one or more plant cells or regions of plant tissue for biotechnological modification.

FIG. 2 is a flow diagram of an example process 200 for identifying one or more plant cells or regions of plant tissue for biotechnological modification. For convenience, the process 200 will be described as being performed by a system of one or more computers located in one or more locations. For example, a high-throughput plant biology system, e.g., the high-throughput plant biology system 100 depicted in FIG. 1, appropriately programmed in accordance with this specification, can perform the process 200.

The system obtains an initial system input characterizing multiple candidate plant cells or multiple candidate regions of plant tissue that are candidates for biotechnological modification (step 202). The initial system input can further characterize one or more desired biotechnological modification to the candidate plant cells or tissue.

The initial system input can include one or more images that depict the candidate plant cells or regions of plant tissue. For example, the initial system input can include a single image containing each candidate plant cell or region of plant tissue, or multiple images each containing one or more candidate plant cells or regions of plant tissue.

The initial system input can also include one or more of: an identification of a developmental stage of the candidate plant cells or tissue; an identification of a type, genus, species, variety, and/or cultivar of the candidate plant cells or tissue; or an identification of the growth conditions (e.g., temperature, humidity, light cycle, timing of some or all of the steps in the protocol, or type of antibiotic) or media (e.g., selection or induction media) used for the candidate plant cells or tissue. In some implementations, each of these identifications can be as a one-hot encoding. That is, each identification can be an embedding that has the same number of elements as the number of possible classes (e.g., the number of developmental stages of plant cells or plant tissue), where the element corresponding to the class of the candidate plant cells or candidate regions of plant tissue is '1' and all other elements are '0.' In some other implementations, the identifications can be encoded in a machine-learned embedding; for example, the embedding can be generated by an embedding neural network that is configured to process the features of the candidate plant cells or tissue to generate a dense embedding.

In this specification, an embedding is an ordered collection of numeric values that represents an input in a particular embedding space. For example, the embedding can be a vector of floating point or other numeric values that has a fixed dimensionality.

The initial system input can also include an embedding of the genotype from which the candidate plant cells or candidate regions of plant tissue originated. For example, the embedding can be a predefined or a machine learned embedding that encodes one or more of: a partial or entire genomic sequence, cisgenes, transgenes, vectors, regulatory elements, resistance markers, single nucleotide polymorphisms, insertions, deletions, or microarray calls.

The initial system input can also include a measure of fitness of the candidate plant cells or candidate regions of plant tissue. Determining the fitness of plant cells or plant tissue is discussed in more detail below in reference to FIG. 6.

The initial system input can also include an embedding of multi-omics data corresponding to the candidate plant cells or candidate regions of plant tissue. Multi-omics data can include information derived from one or more of a: genome, epigenome, transcriptome, proteome, metabolome, lipidome, glycome, cytome, envirome, exome, interferome, kinome, ionome, metalome, methylome, phenome, phytochemome, regulome, or secretome datasets of the plant cells or tissues themselves, the surrounding tissues from which they were derived, or the microbial community surrounding the cells or tissues themselves, or the plants from which they were derived.

After receiving the initial system input, the system processes the initial system input using an initial machine learning model to identify one or more particular plant cells or particular regions of tissue (step 204). The system can select the particular plant cells or particular regions of tissue that the system determines are "biotechnologically-modifiable," i.e., are good candidate for biotechnological modification.

For example, in the implementations in which the initial system input includes one or more images depicting the candidate plant cells or tissue, the system can include a convolutional neural network that is configured to process images of plant cells or plant tissue and identify one or more particular biotechnologically-modifiable plant cells or regions of plant tissue. As a particular example, the convolutional neural network can process images depicting an individual candidate plant cell or candidate region of plant tissue using one or more convolutional neural network layers, and predict a measure of biotechnological modifiability, e.g., a value between 0 and 1. The system can then select a candidate plant cell or region of plant tissue if, e.g., the corresponding measure of biotechnological modifiability surpasses a particular threshold, e.g., 0.5, 0.9, or 0.95. As another particular example, the convolutional neural network can process images depicting multiple candidate plant cells or regions of plant tissue using one or more convolutional neural network layers, and generate an updated image that includes a bounding box surrounding each of one or more biotechnologically-modifiable plant cells or regions of plant tissue.

As another example, in the implementations in which the initial system input includes one or more images each depicting an individual candidate plant cell or region of tissue, the system can generate a embedding for each image, e.g., a Fisher Vector, a vector of locally aggregated descriptors (VLAD), or a scale-invariant feature transform (SIFT) embedding. A Fisher Vector is an embedding of an image that is obtained by pooling local features of the image; see "Image Classification with the Fisher Vector: Theory and Practice," Sanchez et al. (DOI: 10.1007/s11263-013-0636-x) for more details. A VLAD embedding is another embedding of an image that aggregates local features; see "Aggregating Local Descriptors into a Compact Image Representation," Jegou et al. (DOI: 10.1109/CVPR.2010.5540039) for more details). A SIFT embedding extracts a scale-invariant set of keypoints from an image to represent the image; see "Distinctive Image Features from Scale-Invariant Keypoints," Lowe (DOI: 10.1023/B:VISI.0000029664.99615.94) for more details). The system can also generate a machine-learned embedding for each image using a transfer-learned neural network; for example, the system can remove the final one or more neural network layers of a neural network that was trained to perform a different task, and use the output of the modified network as an embedding for the image. As a particular example, the system can use an auto-encoder that has been trained to reconstruct images, or a convolutional neural network that has been trained on different image tasks. Instead or in addition, the system might use a superpixel algorithm to generate an embedding for each image; that is, the system can segment each image into multiple superpixels, encode each superpixel using their type and/or location, and combine the encoding of each superpixel to generate an embedding of the image.

In some implementations, the system can process each image embedding with a machine learning model, e.g., a feedforward network, to predict a measure of biotechnological modifiability for the candidate plant cell or candidate region of plant tissue corresponding to the respective image. In some other implementations, the system can compare each image embedding against each of one or more existing embeddings of images that depict known biotechnologically-modifiable plant cells or regions of plant tissue. As a particular example, the system can compute a difference between the two embeddings; the system can determine that the images corresponding to the embeddings are similar if the distance is less than a predetermined threshold. As another particular example, the system can process the two embeddings with a neural network that is configured to generate a measure of similarity between image embeddings; the system can determine that the images corresponding to the embedding are similar if the measure of similarity exceeds a predetermined threshold. If an image of a candidate plant cell or region of plant tissue is determined to be similar to an existing image of a known biotechnologically-modifiable plant cell or region of plant tissue, then the system can determine the candidate plant cell or region of plant tissue to be biotechnologically-modifiable.

As a particular example, the system can process i) one or more images depicting one or more images each depicting an individual candidate plant cell or region of tissue and ii) one or more images each depicting a known biotechnologically-modifiable plant cell or region of plant tissue using a twin neural network. A twin neural network is a neural network that includes multiple subnetworks that each i) have the same architecture and the same parameter values and ii) process a different input. The twin neural network can process each image and generate an embedding for each. If there multiple images of individual own biotechnologically-modifiable plant cells or regions of plant tissue, then the system can combine the respective embeddings of these images to generate a single embedding corresponding to biotechnologically-modifiable plant cells or tissue, e.g., but computing an average embedding or by processing each respective embedding using a combination neural network. Then, for each particular embedding corresponding to a particular candidate plant cell or region of tissue, the system can compare the particular embedding with the embedding corresponding to biotechnologically-modifiable plant cells or tissue to determine whether the particular candidate plant cell or region of tissue is biotechnologically-modifiable, e.g., by computing a distance between the two embeddings or by processing each embedding using a neural network. Optionally, the system can also process one or more images each depicting a plant cell or region of plant tissue that is known to not be biotechnologically-modifiable, generating a single embedding corresponding to these images as well. In some such implementations, the system can then compare, for each particular embedding corresponding to a particular candidate plant cell or region of tissue, whether the particular embedding is more similar to i) the embedding corresponding to biotechnologically-modifiable cells or tissue or ii) the embedding corresponding to cells or tissue that are not biotechnologically-modifiable, and determine that the particular candidate plant cell or region of tissue belongs to the class whose embedding the particular embedding is more similar to.

As another particular example, the system can determine a boundary, in a particular embedding space, between i) embeddings corresponding to known biotechnologically-modifiable plant cells or regions of tissue and ii) embeddings corresponding to plant cells or regions of tissue that are known not to be biotechnologically-modifiable or are more recalcitrant to being biologically-modifiable. That is, the system can obtain multiple embeddings corresponding to each class, e.g., from results data generated by a modification analysis system after plant cells or regions of tissue are modified, e.g. the modification analysis system 140 depicted in FIG. 1. The embeddings can each be in the same embedding space, and can be generated using images of the respective cells or regions of tissue, other features corresponding to the respective cells or regions of tissue, or both. The system can determine the boundary in the particular embedding space using this labeled data set, e.g., using a support vector machine (SVM) or a multilayer perceptron (MLP).

Referring back to FIG. 2, in response to identifying one or more particular cells or particular regions of tissue, the system can excise or delineate the particular cells or particular regions of tissue (step 206). That is, the system can send commands for an automated external system, e.g., a control system controlling one or more robotic or automated components, to execute the excision or delineation. For example, the external system can excise or delineate the particular cells or particular regions of tissue using one or more of the following techniques: automated colony picking, laser-capture microdissection, laser dissection, optimal slicing, mechanical disruption (e.g., using a blender or some other disruption device), filtration, cell sorting, a hole punch, or full or partial digestion of the cell walls. In some implementations, the selection of the particular protocol for excising or delineating the particular cells or particular regions of tissue can itself be machine-learned, according to the received initial system input and/or data characterizing the identified particular cells or particular regions of tissue, e.g., images of the identified particular cells or particular regions of tissue. Example techniques for determining a protocol are discussed in more detail below in reference to FIG. 3; although the protocol whose determination is discussed in FIG. 3 is a different protocol, namely, a protocol for delivering exogenous material instead of a protocol for excising or delineating plant cells or tissue, similar machine learning methods can be applied to determine both protocols.

The system can then deliver exogenous material to the excised or delineated cells or regions of tissue (step 208). That is, the system can send commands to an automated external system, e.g., a control system controlling one or more robotic or automated components, to deliver the exogenous material. For example, the external system can deliver exogenous genetic material to the genome of the excised or delineated plant cells or regions of tissue. As another example, the external system can edit the RNA of the excised or delineated plant cells or plant tissue. As another example, the external system can deliver exogenous proteins or other biomolecules to the excised or delineated plant cells or plant tissue. The system can also send commands to the automated system to prepare the excised or delineated cells or regions of tissue before delivering the exogenous material; for example, the system can send commands to place the cells or tissue on a particular medium in a particular set of conditions, or transfer the cells or tissue between multiple media to prepare the cells or tissue.

Figure 3:
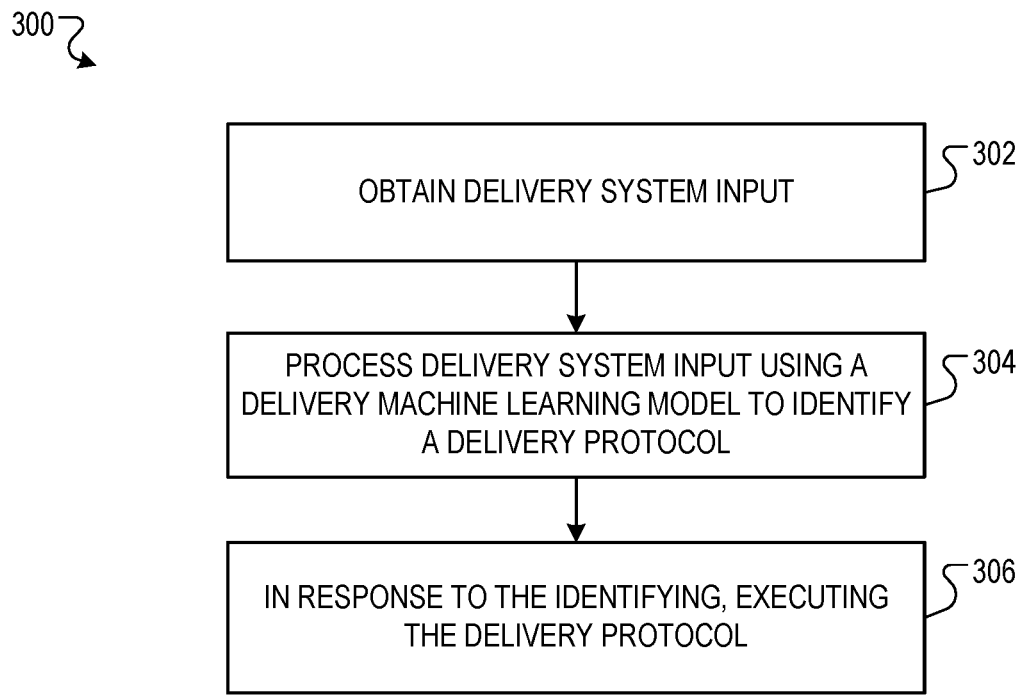
FIG. 3 is a flow diagram of an example process for identifying one or more protocols for delivering exogenous material to one or more plant cells or plant tissue.

FIG. 3 is a flow diagram of an example process 300 for identifying one or more protocols for delivering exogenous material to one or more plant cells or plant tissue. For convenience, the process 300 will be described as being performed by a system of one or more computers located in one or more locations. For example, a high-throughput plant biology system, e.g., the high-throughput plant biology system 100 depicted in FIG. 1, appropriately programmed in accordance with this specification, can perform the process 300.

The system obtains a delivery system input (step 302). The delivery system input can characterize i) one or more plant cells or regions of plant tissue that are to be biotechnologically modified, ii) one or more desired biotechnological modification to the plant cells or tissue, or iii) both.

For example, the delivery system input can include one or more of: one or more images depicting the plant cells or regions of plant tissue; an identification of a type of the plant cells or tissue; an identification of a developmental stage of the plant cells or tissue; an identification of a genus, species, variety, and/or cultivar of the plant cells or tissue; an identification of the growth conditions or selection media used for the plant cells or tissue; an embedding of the genotype of the plant cells or regions of plant tissue; a measure of fitness of the plant cells or regions of plant tissue; or an embedding of multi-omics data corresponding to the plant cells or regions of plant tissue.

The delivery system input can also include an embedding of the one or more desired biotechnological modifications, e.g., a one-hot embedding corresponding to a particular biotechnological modification, e.g., genetic engineering, RNA insertion or deletion, protein delivery, etc.

After receiving the delivery system input, the system can process the delivery system input using a delivery machine learning model to identify a particular delivery protocol for delivering the exogenous material according to the one or more desired biotechnological modifications (step 304).

For example, the particular delivery protocol can be one or more of: bacterial delivery of the exogenous material; viral delivery of the exogenous material; chemical delivery of the exogenous material, e.g., polyethylene glycol (PEG); biolistics, e.g., a gene gun; nanoparticles; or microinjection.

In some implementations, the delivery machine learning model includes a feedforward neural network that is configured to process delivery system inputs to determine a particular delivery protocol. For example, the output of the feedforward neural network can include the same number of elements as the number of possible delivery protocols, and the system can determine to execute the delivery protocol corresponding to the element with the highest value in the output of the feedforward neural network. In the implementations in which the delivery system input include one or more images, the feedforward neural network can include a convolutional subnetwork of one or more convolutional neural network layers that can process the one or more images.

In some implementations, the delivery machine learning model is a reinforcement learning model. For example the delivery machine learning model can be trained using a reinforcement learning objective function generated from the output of a modification analysis system, e.g., the modification analysis system 140 depicted in FIG. 1, that processes biotechnologically modified cells or tissues to determine a measure of success of the biotechnological modification, e.g., a modification efficiency.

For example, the delivery machine learning model can use one or more of the following reinforcement learning algorithms: Q-Learning, Value Iteration, Policy Iteration, Proximal Policy Optimization (PPO), a Monte Carlo method, or a Deep Q-Network (DQN). As a particular example, using a Deep Q-Network, the system can train a neural network, e.g., a feedforward neural network or a convolutional neural network, to approximate a Q-Value for a particular delivery system input and a particular delivery protocol.

In response to identifying the delivery protocol, the system executes the delivery protocol (step 306). That is, the system can send commands for an automated external system, e.g., a control system controlling one or more robotic or automated components, to deliver the exogenous material.

Figure 4:
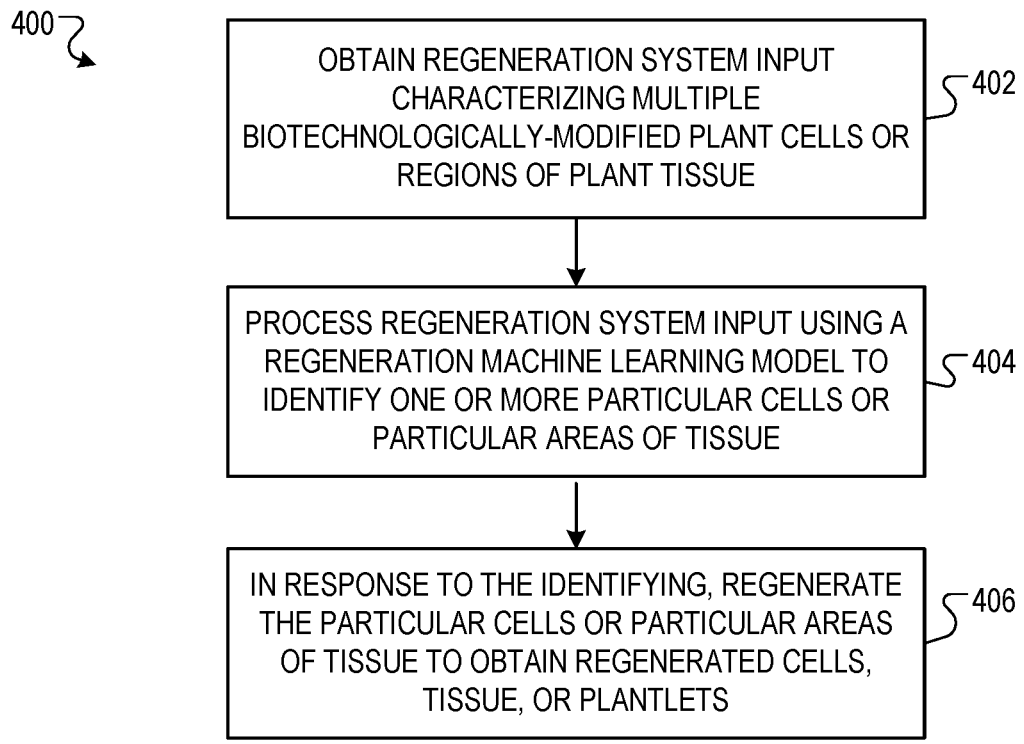
FIG. 4 is a flow diagram of an example process for identifying one or more modified plant cells or modified regions of plant tissue for regeneration.

FIG. 4 is a flow diagram of an example process 400 for identifying one or more modified plant cells or modified regions of plant tissue for regeneration. For convenience, the process 400 will be described as being performed by a system of one or more computers located in one or more locations. For example, a high-throughput plant biology system, e.g., the high-throughput plant biology system 100 depicted in FIG. 1, appropriately programmed in accordance with this specification, can perform the process 400.

The system obtains a regeneration system input characterizing multiple biotechnologically-modified plant cells or regions of plant tissue that are candidates for regeneration. The system input can further characterize one or more biotechnological modifications that were performed on the plant cells or tissue.

The regeneration system input can include one or more images that depict the biotechnologically-modified plant cells or regions of plant tissue. For example, the regeneration system input can include a single image containing each plant cell or region of plant tissue, or multiple images each containing one or more plant cells or regions of plant tissue.

The regeneration system input can also include one or more of: an identification of a type of the biotechnologically-modified plant cells or tissue; an identification of a developmental stage of the biotechnologically-modified plant cells or tissue; an identification of a genus, species, variety, and/or cultivar of the biotechnologically-modified plant cells or tissue; or an identification of the growth conditions or selection media used for the candidate plant cells or tissue. For example, each of these identifications can be a one-hot encoding or a dense machine-learned embedding.

The regeneration system input can also include one or more of: an embedding of the genotype of the biotechnologically-modified plant cells or candidate regions of plant tissue; a measure of fitness of the biotechnologically-modified plant cells or candidate regions of plant tissue; or an embedding of multi-omics data corresponding to the biotechnologically-modified plant cells or regions of plant tissue.

After receiving the regeneration system input, the system can process the regeneration system input using a regeneration machine learning model to identify one or more particular biotechnologically-modified cells or regions of tissue (step 404). The system can select the particular plant cells or regions of tissue that the system determines are "regenerable," i.e., are good candidates for regeneration.

Example regeneration machine learning models can include similar machine learning models to those described above in reference to FIG. 2 for identifying plant cells or regions of tissue for biotechnological modification. For example, the regeneration machine learning model can include a convolutional neural network that is configured to process images of biotechnologically-modified plant cells or plant tissue and identify one or more particular regenerable plant cells or regions of plant tissue.

As another example, the regeneration machine learning model can process images each depicting an individual biotechnologically-modified plant cell or regions of tissue to generate an embedding for each image, e.g., a Fisher Vector, a vector of locally aggregated descriptors (VLAD), or a scale-invariant feature transform (SIFT) embedding. The system can then process each image embedding with a machine learning model, e.g., a feedforward network, to predict a measure of regenerability for the biotechnologically-modified plant cell or region of plant tissue corresponding to the respective image; or, the system can compare each image embedding against each of one or more existing embeddings of images that depict known regenerable plant cells or regions of plant tissue. As a particular example, the system can use determine a boundary, in a particular embedding space, between i) embeddings corresponding to known regenerable plant cells or regions of tissue and ii) plant cells or regions of tissue that are known not to be regenerable, e.g., using a support vector machine (SVM) or a multilayer perceptron (MLP).

Referring back to FIG. 4, in response to identifying one or more particular biotechnologically-modified cells or regions of tissue, the system can regenerate the particular cells or regions of tissue to obtain regenerated cells, tissue, or plantlets (step 406). That is, the system can send commands for an automated external system, e.g., a control system controlling one or more robotic or automated components, to perform the regeneration. For example, the external system can regenerate the particular cells or regions of tissue using one or more of the following techniques: identification and separation, e.g., through laser dissection, of independent events or plantlets, e.g., independent regeneration events in the same callus; induction or regulation of developmental genes, e.g., native or heterologous genes; hormones, e.g., shoot or root induction or organogenesis; selection or screening of the biotechnologically-modified plant cells or regions of plant tissue before executing regeneration; selection or screening of regenerated plant cells, regions of plant tissue, or plantlets after execution regeneration; laser dissection of the particular cells or regions of tissue before executing regeneration; or the use of fluorescence or indicator markers as guidance. Regenerating the particular cells or regions of tissue can also require a determination of culture conditions, e.g., a media selection, light intensity and duration, or gas concentrations; or a determination of a timing and order of different culturing steps, which can be optimized by this process as well. This model may also be able to improve the inputs to any of the previous processes, such as optimizing the genetic sequence of desired transgene insertion for maximum transformation efficiency, optimizing delivery protocols, etc.

In some implementations, the selection of the particular regeneration protocol can be machine-learned, according to the received regeneration system input and/or data characterizing the identified biotechnologically-modified cells or particular regions of tissue. Example techniques for determining a protocol are discussed above in more detail below in reference to FIG. 3; although the protocol whose determination is discussed in FIG. 3 is a different protocol, namely, a protocol for delivering exogenous material instead of a protocol for regenerating plant cells or tissue, similar machine learning methods can be applied to determine both protocols.

Figure 5:
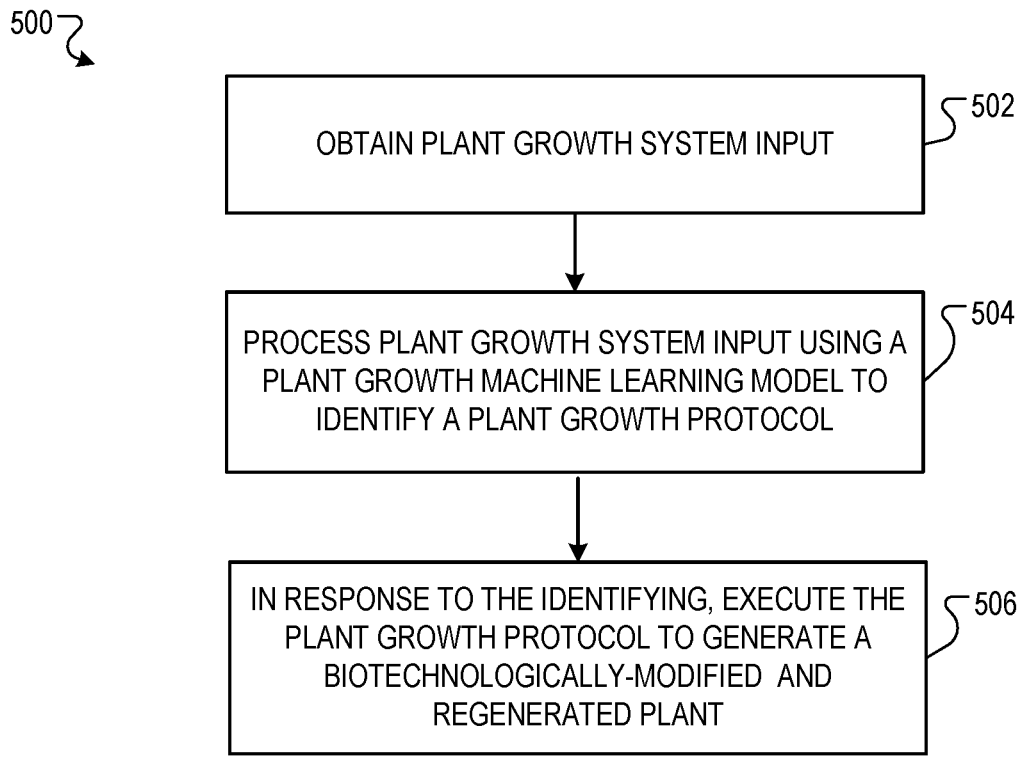
FIG. 5 is a flow diagram of an example process for identifying one or more protocols for growing regenerated plant cells or plant tissue into a plant.

FIG. 5 is a flow diagram of an example process 500 for identifying one or more protocols for growing regenerated plant cells or plant tissue into a plant. For convenience, the process 500 will be described as being performed by a system of one or more computers located in one or more locations. For example, a high-throughput plant biology system, e.g., the high-throughput plant biology system 100 depicted in FIG. 1, appropriately programmed in accordance with this specification, can perform the process 500.

The system obtains a plant growth system input (step 502). The plant growth system input can characterize i) one or more regenerated plant cells or regions of plant tissue that are to be grown into a plant, ii) one or more biotechnological modifications to the regenerated plant cells or tissue, or iii) both.

For example, the plant growth system input can include one or more of: one or more images depicting the regenerated plant cells or regions of plant tissue; an identification of a type of the regenerated plant cells or tissue; an identification of a developmental stage of the regenerated plant cells or tissue; an identification of a genus, species, variety, and/or cultivar of the regenerated plant cells or tissue; an identification of the growth conditions or selection media used for the regenerated plant cells or tissue; an embedding of the genotype of the regenerated plant cells or regions of plant tissue; a measure of fitness of the regenerated plant cells or regions of plant tissue; an embedding of multi-omics data corresponding to the regenerated plant cells or regions of plant tissue; or any of the experimental parameters that precede the regeneration step.

The plant growth system input can also include one or more of: a detection of an expression of one or more reporter genes in the regenerated plant cells or tissue or the results of a genetic analysis of the regenerated plant cells or tissue. For example, the data in the plant growth system input can be obtained using one or more of the following techniques: detection of a protein, e.g., through mass spectrometry, chromatography, ELISA or FISH; phenotyping, including multi-omics analysis; detection of nucleic acid, e.g., through microarrays, PCR or sequencing; chromatography; mass spectrometry; or an enzymatic or metabolic assay.

After receiving the plant growth system input, the system can process the plant growth system input using a plant growth machine learning model to identify a particular plant growth protocol for growing the regenerated plant cells or tissue into a plant (step 504).

For example, the particular delivery protocol can include a determination of one or more of the following: a concentration of media components, e.g., a concentration of hormones; a duration or order of individual plant growth steps; a light cycling intensity; or gas concentrations, e.g., $CO_2$ or $H_2O$.

In some implementations, the plant growth machine learning model includes a feedforward neural network that is configured to process plant growth system inputs to determine a particular plant growth protocol. In the implementations in which the plant growth system input includes one or more images, the feedforward neural network can include a convolutional subnetwork of one or more convolutional neural network layers that can process the one or more images.

In some implementations, the plant growth machine learning model is a reinforcement learning model. For example the plant growth machine learning model can be trained using a reinforcement learning objective function generated from the output of a plant growth analysis system, e.g., the plant growth analysis system 194 depicted in FIG. 1, that processes engineered and regenerated plants to determine a measure of success of the plant growth, e.g., a plant growth efficiency.

In some implementations, the system can select one or more candidate regenerated cells or tissues to process using the plant growth protocol, using one or more machine learning models. For example, the system can use one or more machine learning models similar to those described above in reference to FIG. 4 for selecting biotechnologically-modified cells or tissue for regeneration.

In response to identifying the plant growth protocol, the system executes the plant growth protocol (step 306). That is, the system can send commands for an automated external system, e.g., a control system controlling one or more robotic or automated components, to grow the regenerated cells or tissue.

Figure 6:
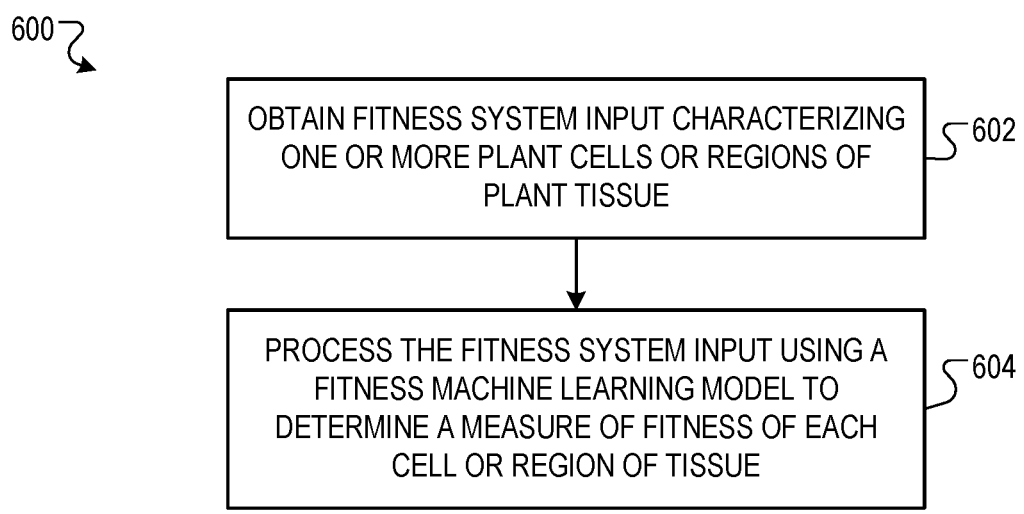
FIG. 6 is a flow diagram of an example process for determining a measure of fitness of a plant cell or region of plant tissue.

FIG. 6 is a flow diagram of an example process 600 for determining a measure of fitness of a plant cell or region of plant tissue. For convenience, the process 600 will be described as being performed by a system of one or more computers located in one or more locations. For example, a high-throughput plant biology system, e.g., the high-throughput plant biology system 100 depicted in FIG. 1, appropriately programmed in accordance with this specification, can perform the process 600.

The system obtains a fitness system input corresponding to one or more plant cells or regions of plant tissue (step 602). The fitness system input can include one or more images of the plant cells or tissues. The plant cells or tissues can be cells or tissue that have not yet been biotechnologically modified, or they can be cells or tissue that are in any stage of a biotechnological modification process or regeneration. The fitness system input can also include data obtained using one or more of the following techniques: multi-omic analysis, multi-spectral or hyperspectral imaging; microscopy or morphology; staining, e.g., staining using acridine orange, eosin, giemsa, or hematoxylin; or assay, e.g., colorimetric, chemiluminescence, or apoptosis assays.

The system processes the fitness system input using a fitness machine learning model to determine a measure of fitness of each plant cell or region of plant tissue (step 604). For example, the fitness machine learning model can include a feedforward network that is configured to process fitness system inputs to determine a fitness of the plant cells or tissue, e.g., a value between 0 and 1. In the implementations in which the fitness system input include one or more images, the feedforward neural network can include a convolutional subnetwork of one or more convolutional neural network layers that can process the one or more images.

Figure 7:
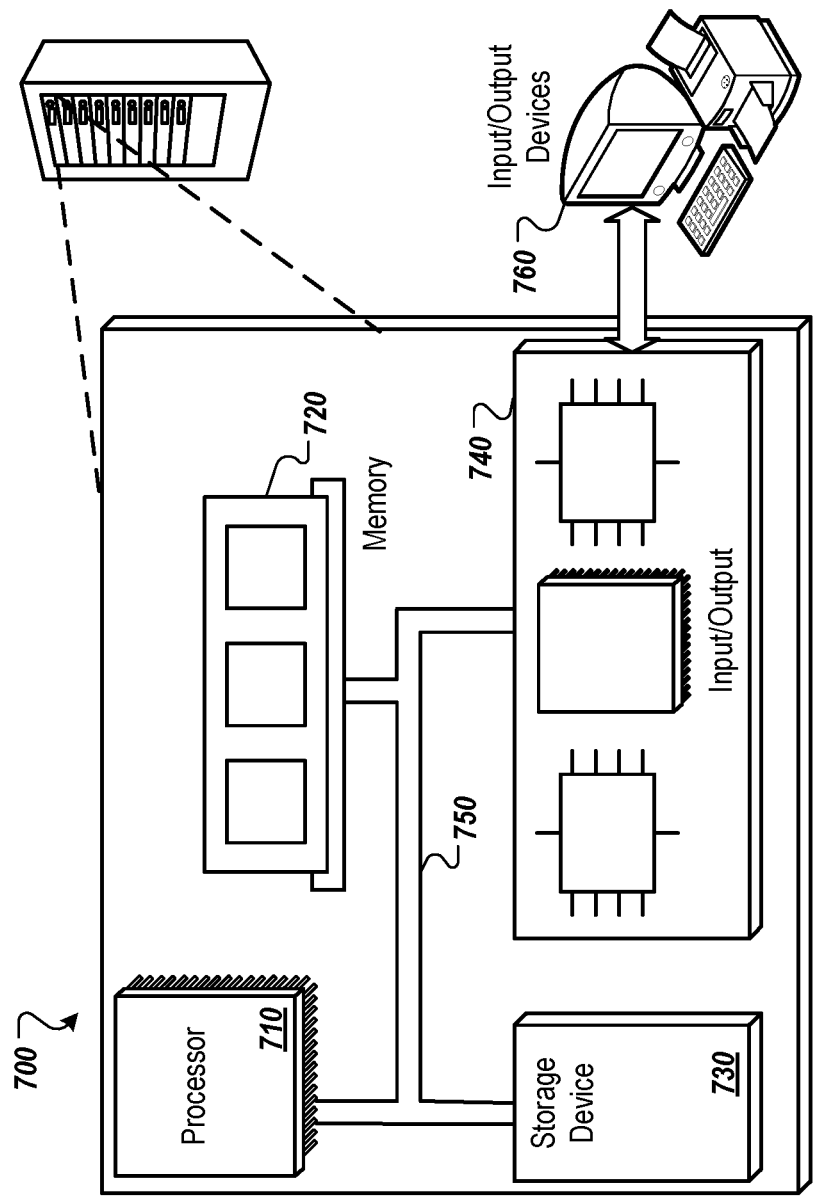
FIG. 7 is a block diagram of an example computer system.

FIG. 7 is a block diagram of an example computer system 700 that can be used to perform operations described above. The system 700 includes a processor 710, a memory 720, a storage device 730, and an input/output device 740. Each of the components 710, 720, 730, and 740 can be interconnected, for example, using a system bus 750. The processor 710 is capable of processing instructions for execution within the system 700. In one implementation, the processor 710 is a single-threaded processor. In another implementation, the processor 710 is a multi-threaded processor. The processor 710 is capable of processing instructions stored in the memory 720 or on the storage device 730.

The memory 720 stores information within the system 700. In one implementation, the memory 720 is a computer-readable medium. In one implementation, the memory 720 is a volatile memory unit. In another implementation, the memory 720 is a non-volatile memory unit.

The storage device 730 is capable of providing mass storage for the system 700. In one implementation, the storage device 730 is a computer-readable medium. In various different implementations, the storage device 730 can include, for example, a hard disk device, an optical disk device, a storage device that is shared over a network by multiple computing devices (for example, a cloud storage device), or some other large capacity storage device.

The input/output device 740 provides input/output operations for the system 700. In one implementation, the input/output device 740 can include one or more network interface devices, for example, an Ethernet card, a serial communication device, for example, a RS-232 port, and/or a wireless interface device, for example, a 802.11 card. In another implementation, the input/output device can include driver devices configured to receive input data and send output data to other input/output devices, for example, keyboard, printer and display devices 760. Other implementations, however, can also be used, such as mobile computing devices, mobile communication devices, set-top box television client devices, etc.

Although an example processing system has been described in FIG. 7, implementations of the subject matter and the functional operations described in this specification can be implemented in other types of digital electronic circuitry, or in computer software, firmware, or hardware, including the structures disclosed in this specification and their structural equivalents, or in combinations of one or more of them.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, off-the-shelf or custom-made parallel processing subsystems, e.g., a GPU or another kind of special-purpose processing subsystem. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program which may also be referred to or described as a program, software, a software application, an app, a module, a software module, a script, or code) can be written in any form of programming language, including compiled or interpreted languages, or declarative or procedural languages, and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and pointing device, e.g, a mouse, trackball, or a presence sensitive display or other surface by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone, running a messaging application, and receiving responsive messages from the user in return.

Embodiments of the subject matter described in this specification can be implemented in a computing system that includes a back end component, e.g., as a data server, or that includes a middleware component, e.g., an application server, or that includes a front end component, e.g., a client computer having a graphical user interface, a web browser, or an app through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML, page, to a user device, e.g., for purposes of displaying data to and receiving user input from a user interacting with the device, which acts as a client. Data generated at the user device, e.g., a result of the user interaction, can be received at the server from the device.

In addition to the embodiments described above, the following embodiments are also innovative:

Embodiment 1 is a method comprising:
  obtaining a network input comprising an image depicting a plurality of plant cells or regions of plant tissue;
  processing the network input using a machine learning model to obtain an identification of one or more particular biotechnologically-modifiable plant cells or one or more particular biotechnologically-modifiable regions of the plant tissue;
  excising or delineating the one or more identified plant cells or the one or more identified regions of the plant tissue; and
  delivering exogenous material to the excised or delineated plant cells or regions of plant tissue.

Embodiment 2 is the method of embodiment 1, wherein the network input includes one or more images depicting the plurality of plant cells or plant tissue; and
  processing the network input using a machine learning model comprises processing the one or more images using a convolutional neural network that has been configured through training to:
    receive a network input comprising one or more images of a plurality of plant cells or plant tissue, and
    process the network input to generate an identification of one or more particular biotechnologically-modifiable plant cells or one or more particular biotechnologically-modifiable regions of plant tissue.

Embodiment 3 is the method of any one of embodiments 1 or 2, wherein delivering exogenous material to the excised or delineated plant cells or regions of plant tissue comprises one or more of:
  genetically engineering the excised or delineated plant cells or regions of plant tissue;
  editing the RNA of the excised or delineated plant cells or regions of plant tissue; or
  delivering proteins to the excised or delineated plant cells or regions of plant tissue.

Embodiment 4 is the method of any one of embodiments 1-3, wherein the network input further comprises one or more of:
  an identification of a type of the plant cells or plant tissue;
  an identification of a developmental stage of the plant cells or plant tissue;
  an identification of a genus, species, variety, or cultivar of the plant cells or plant tissue;
  an embedding of a genotype of the plant cells or tissue; or
  a measure of fitness of the plant cells or tissue;
  an identification of the growth conditions and selection media used; or
  multi-omics data.

Embodiment 5 is the method of any one of embodiments 1-4, wherein the identification of the one or more particular biotechnologically-modifiable plant cells or one or more particular biotechnologically-modifiable regions of the plant tissue comprises an updated image depicting the plurality of plant cells or plant tissue, wherein the updated image comprises a bounding box surrounding each of the one or more particular biotechnologically-modifiable plant cells or the one or more particular biotechnologically-modifiable regions of plant tissue.

Embodiment 6 is the method of any one of embodiments 1-5, wherein excising or delineating the one or more identified plant cells or the one or more identified regions of the plant tissue comprises one or more of:
- automated colony picking;
- laser dissection;
- laser-capture microdissection;
- optimal slicing;
- mechanical disruption;
- filtration;
- cell sorting;
- using a hole punch; or
- full or partial digestion of a cell wall of the identified plant cells or regions of plant tissue.

Embodiment 7 is the method of any one of embodiments 1-6, wherein one or more techniques for excising or delineating the one or more identified plant cells are selected using machine learning.

Embodiment 8 is the method of any one of embodiments 1-7, wherein delivering exogenous material to the excised or delineated plant cells or regions of plant tissue comprises sending instructions to one or more automated components to execute operations comprising one or more of:
- separating independent biotechnologically-modifiable cells or tissue; or
- moving one or more of the plant cells or regions of tissue to different media.

Embodiment 9 is a method comprising:
- obtaining data characterizing one or more plant cells or plant tissue;
- processing a network input generated from the data using a machine learning model to obtain an identification of one or more delivery protocols, wherein the machine learning model has been configured through training to:
  - receive a network input corresponding to a one or more plant cells or plant tissue, and
  - process the network input to generate an identification of one or more delivery methods for delivering exogenous material to the one or more plant cells or plant tissue; and
- performing the one or more identified delivery methods using the one or more plant cells or plant tissue.

Embodiment 10 is the method of embodiment 9, wherein the data characterizing the one or more plant cells or plant tissue comprises:
- an identification of a type of the plant cells or plant tissue;
- an identification of a developmental stage of the plant cells or plant tissue;
- an identification of growth conditions of the plant cells or plant tissue;
- an identification of a genus, species, variety, or cultivar of the plant cells or plant tissue;
- multi-omics data; or
- a measure of fitness of the plant cells or tissue.

Embodiment 11 is the method of any one of embodiments 9 or 10, wherein the one or more identified delivery methods comprise one or more of:
- bacterial delivery;
- viral delivery;
- chemical delivery;
- biolistics;
- nanoparticles; or
- microinjection.

Embodiment 12 is a method comprising:
- obtaining a network input characterizing one or more of biotechnologically-modified plant cells or biotechnologically-modified regions of plant tissue;
- processing the network input using a machine learning model to obtain an identification of one or more particular regenerable biotechnologically-modified plant cells or one or more particular regions of regenerable biotechnologically-modified plant tissue;
- performing one or more regeneration techniques using the one or more identified regenerable biotechnologically-modified plant cells or the one or more identified regions of the regenerable biotechnologically-modified plant tissue.

Embodiment 13 is the method of embodiment 12, wherein:
- the network input comprises one or more images depicting a plurality of biotechnologically-modified plant cells or biotechnologically-modified regions of plant tissue; and
- processing the network input using a machine learning model comprises processing the one or more images using a convolutional neural network that has been configured through training to:
  - receive a network input comprising one or more images of a plurality of biotechnologically-modified plant cells or biotechnologically-modified plant tissue, and
  - process the network input to generate an identification of one or more regenerable biotechnologically-modified plant cells or one or more regenerable biotechnologically-modified regions of plant tissue.

Embodiment 14 is the method of any one of embodiments 12 or 13, wherein the network input further comprises:
- an identification of a type of the biotechnologically-modified plant cells or biotechnologically-modified plant tissue;
- an identification of a developmental stage of the biotechnologically-modified plant cells or biotechnologically-modified plant tissue;
- an identification of a genus, species, variety, or cultivar of the biotechnologically-modified plant cells or biotechnologically-modified plant tissue;
- an identification of the growth conditions or selection media used;
- a measure of fitness of the biotechnologically-modified plant cells or biotechnologically-modified tissue; or
- multi-omics data.

Embodiment 15 is the method of any one of embodiments 12-14, wherein the one or more regeneration techniques comprise one or more of:
- laser dissection of the biotechnologically modified plant cells or regions of plant tissue before regeneration;
- transferring, using one or more automation components, one or more of the biotechnologically modified plant cells or regions of plant tissue between different media;
- laser dissection of multiple regeneration events after regenerating the one or more regenerable biotechnologically modified plant cells or regions of plant tissue;
- determining culture conditions;
- determining a timing and order of different culturing steps;
- separation of independent events or plantlets;
- induction or regulation of developmental genes;
- hormones;
- selection or screening of plant cells or regions of plant tissue before regeneration;
- selection or screening of plant cells, regions of plant tissue, or plantlets after regeneration; or
- use of fluorescence or indicator markers as guidance.

Embodiment 16 is the method of any one of embodiments 12-15, wherein the one or more regeneration techniques are selected using a machine learning model.

Embodiment 17 is a method comprising:
obtaining data characterizing a one or more regenerated plant cells or regenerated plant tissue;
processing a network input generated from the data using a machine learning model to obtain an identification of one or more plant growth methods, wherein the machine learning model has been configured through training to:
receive a network input corresponding to a one or more regenerated plant cells or regenerated plant tissue, and
process the network input to generate an identification of one or more plant growth methods for growing the one or more regenerated plant cells or regenerated plant tissue; and
performing the one or more identified plant growth methods using the one or more regenerated plant cells or regenerated plant tissue to generate a plant from the regenerated plant cells or regenerated plant tissue.

Embodiment 18 is the method of embodiment 17, wherein the data characterizing the one or more regenerated plant cells or regenerated plant tissue comprises one or more of:
a detection of an expression of a reporter gene;
results of a genetic analysis;
selection/screening;
results of a multi-omic analysis; or
a measure of fitness of the regenerated plant cells or regenerated plant tissue, the mature plant, or its progeny.

Embodiment 19 is the method of any one of embodiments 17 or 18, wherein the data characterizing the one or more regenerated plant cells or regenerated plant tissue has been obtaining using one or more of:
detection of protein;
detection of a metabolite;
phenotyping for a desired output;
multi-omic analysis;
detection of nucleic acid; or enzymatic/metabolic assay.

Embodiment 20 is the method of any one of embodiments 17-19, wherein the one or more plant growth methods comprise one or more of:
a determination of a concentration of media components;
a determination of a duration of individual steps;
a determination of an order of individual steps;
a light cycling intensity; or
a determination of gas concentrations.

Embodiment 21 is a system comprising: one or more computers and one or more storage devices storing instructions that are operable, when executed by the one or more computers, to cause the one or more computers to perform the method of any one of embodiments 1 to 20.

Embodiment 22 is a computer storage medium encoded with a computer program, the program comprising instructions that are operable, when executed by data processing apparatus, to cause the data processing apparatus to perform the method of any one of embodiments 1 to 20.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain some cases, multitasking and parallel processing may be advantageous.

What is claimed is:

1. A method comprising:
obtaining an image depicting a collection of one or more biotechnologically-modified plant cells;
selecting one or more plant cells from the collection of biotechnologically-modified plant cells for regeneration, comprising:
processing a machine learning model input that comprises the image depicting the collection of one or more biotechnologically-modified plant cells using an image processing machine learning model to generate a machine learning model output that characterizes a predicted capacity of regeneration of plant cells in the collection of biotechnologically-modified plant cells; and
selecting one or more plant cells from the collection of biotechnologically-modified plant cells for regeneration based on the machine learning model output that characterizes the predicted capacity of regeneration of plant cells in the collection of biotechnologically-modified plant cells.

2. The method of claim 1, further comprising:
applying a plant regeneration protocol to one or more plant cells selected for regeneration based on the machine learning model output.

3. The method of claim 1, wherein the machine learning model comprises a neural network model.

4. The method of claim 3, wherein the neural network model comprises one or more convolutional neural network layers.

5. The method of claim 1, wherein the machine learning model comprises a set of machine learning model parameters that have been trained using a machine learning training technique.

6. The method of claim 1, wherein the machine learning model input further comprises:
data identifying a type of the biotechnologically-modified plant cells.

7. The method of claim 1, wherein the machine learning model input further comprises:
data identifying a developmental stage of the biotechnologically-modified plant cells.

8. The method of claim 1, wherein the machine learning model input further comprises:
data identifying a genus, species, variety, or cultivar of the biotechnologically-modified plant cells.

9. The method of claim 1, wherein the machine learning model input further comprises:
data identifying growth conditions or selection media associated with the collection of biotechnologically-modified plant cells.

10. The method of claim 1, wherein the machine learning model input further comprises:
data identifying a measure of fitness of the biotechnologically-modified plant cells.

11. The method of claim 1, wherein the machine learning model input further comprises:
multi-omics data characterizing the biotechnologically-modified plant cells.

12. The method of claim 1, further comprising:
selecting a plant regeneration protocol to apply to the one or more plant cells selected for regeneration using a protocol selection model.

13. The method of claim 12, wherein the protocol selection model comprises a machine learning model.

14. The method of claim 12, wherein selecting a plant regeneration protocol to apply to the one or more plant cells selected for regeneration using a protocol selection model comprises:
processing a model input that characterizes the one or more plant cells selected for regeneration using the protocol selection model to generate a model output; and
selecting the plant regeneration protocol to apply to the one or more plant cells selected for regeneration using the model output of the protocol selection model.

15. The method of claim 14, wherein the selected plant regeneration protocol specifies a plant regeneration apparatus.

16. The method of claim 14, wherein the selected plant regeneration protocol specifies a plant regeneration technique.

17. The method of claim 12, further comprising:
evaluating of regeneration efficiency resulting from applying the selected plant regeneration protocol to the one or more plant cells selected for regeneration.

18. A system comprising:
one or more computers; and
one or more storage devices communicatively coupled to the one or more computers, wherein the one or more storage devices store instructions that, when executed by the one or more computers, cause the one or more computers to perform operations comprising:
obtaining an image depicting a collection of one or more biotechnologically-modified plant cells;
selecting one or more plant cells from the collection of biotechnologically-modified plant cells for regeneration, comprising:
processing a machine learning model input that comprises the image depicting the collection of one or more biotechnologically-modified plant cells using an image processing machine learning model to generate a machine learning model output that characterizes a predicted capacity of regeneration of plant cells in the collection of biotechnologically-modified plant cells; and
selecting one or more plant cells from the collection of biotechnologically-modified plant cells for regeneration based on the machine learning model output that characterizes the predicted capacity of regeneration of plant cells in the collection of biotechnologically-modified plant cells.

19. One or more non-transitory computer storage media storing instructions that when executed by one or more computers cause the one or more computers to perform operations comprising:
obtaining an image depicting a collection of one or more biotechnologically-modified plant cells;
selecting one or more plant cells from the collection of biotechnologically-modified plant cells for regeneration, comprising:
processing a machine learning model input that comprises the image depicting the collection of one or more biotechnologically-modified plant cells using an image processing machine learning model to generate a machine learning model output that characterizes a predicted capacity of regeneration of plant cells in the collection of biotechnologically-modified plant cells; and
selecting one or more plant cells from the collection of biotechnologically-modified plant cells for regeneration based on the machine learning model output that characterizes the predicted capacity of regeneration of plant cells in the collection of biotechnologically-modified plant cells.

20. The one or more non-transitory computer storage media of claim 19, wherein the operations further comprise:
applying a plant regeneration protocol to one or more plant cells selected for regeneration based on the machine learning model output.

* * * * *